(12) United States Patent
Duran Von Arx

(10) Patent No.: US 7,775,794 B2
(45) Date of Patent: Aug. 17, 2010

(54) MECHANICAL DEVICE FOR USE IN ORTHODONTICS

(76) Inventor: Josep Duran Von Arx, Paseo de Valldaura 220-1°-1a, Barcelona, Barcelona (ES) 08031

( * ) Notice: Subject to any disclaimer, the term of this patent is extended or adjusted under 35 U.S.C. 154(b) by 678 days.

(21) Appl. No.: 11/658,506

(22) PCT Filed: Jul. 29, 2004

(86) PCT No.: PCT/ES2004/000354

§ 371 (c)(1),
(2), (4) Date: Jan. 25, 2007

(87) PCT Pub. No.: WO2006/030033

PCT Pub. Date: Mar. 23, 2006

(65) Prior Publication Data

US 2009/0011381 A1    Jan. 8, 2009

(51) Int. Cl.
*A61C 3/00*    (2006.01)
(52) U.S. Cl. ........................................................ 433/10
(58) Field of Classification Search ................ 433/8–18
See application file for complete search history.

(56) References Cited

U.S. PATENT DOCUMENTS

| | | | | | |
|---|---|---|---|---|---|
| 4,527,975 | A | * | 7/1985 | Ghafari et al. ................. | 433/8 |
| 4,597,739 | A | * | 7/1986 | Rosenberg .................... | 433/16 |
| 5,160,260 | A | * | 11/1992 | Chang ........................... | 433/8 |
| 6,206,690 | B1 | * | 3/2001 | Vargas ........................... | 433/9 |
| 7,025,591 | B1 | * | 4/2006 | Kesling ........................ | 433/10 |
| 7,033,170 | B2 | * | 4/2006 | Cordato ........................ | 433/10 |
| 2002/0006595 | A1 | * | 1/2002 | Voudouris ....................... | 433/4 |

* cited by examiner

*Primary Examiner*—Cris L Rodriguez
*Assistant Examiner*—Heidi M Eide
(74) *Attorney, Agent, or Firm*—Porzio, Bromberg & Newman, P.C.

(57) ABSTRACT

The invention relates to a mechanical device for use in orthodontics. The inventive device has a base (2) which is cemented onto a tooth (1) and a cap or closure element (3) which is mounted on the base (2).

According to the invention, the device has the following functional characteristics: an orthodontic wire insertion groove which is provided on the cap or closure element instead of at the base of the bracket as is usual; the adjustment of the wire by means of a pull mechanism which is provided on the cap or closure element; a self-closing system for the wire; an aesthetic, functional design with minimum friction on soft tissues (lips); customization of the torque and the tip, such that suitable values can be applied according to the requirements of each case and treatment phase; and minimization of the time required to adjust arcs in the mouth.

11 Claims, 5 Drawing Sheets

MECHANICAL DEVICE FOR USE IN ORTHODONTICS

CROSS REFERENCE TO RELATED APPLICATION

This is a National Stage of International Application No. PCT/ES2004/000354, filed Jul. 29, 2004, the disclosures of which Application is incorporated by reference herein.

OBJECT OF THE INVENTION

The object of the invention is to provide a mechanical device for use in orthodontics, whose functional characteristics are of the following:
- an orthodontic wire insertion groove which is provided on the cap or closure element instead of at the base of the bracket as it is usual;
- adjustment of the wire by means of a pull mechanism which is included on the cap or closure element;
- a self-closing mechanism system of the wire;
- an aesthetic, functional design with minimum friction on soft tissues (lips).
- customisation of the torque and the tip, such that this suitable values can be applied according to the requirements of each case and treatment phase;
- minimisation of the time required to adjust archs in the mouth.

BACKGROUND OF THE INVENTION

In orthodontics, devices are used to transfer the forces produced by the wires on the teeth, with the aim to move the teeth and correct in this way the wrong dental positions of the patient.

The devices used nowadays may be either metallic or else be made of materials with a more aesthetic appearance (with a colour similar to the one of the teeth). At the present time, these devices have basically a single piece, called generally the base, as it shows a horizontal groove on which the corrector wire is introduced. The fixation of the wire inside the groove of the device is done by means of metallic or elastic ties that join both devices. The groove actually used shows a width of 0.18 inches, or 0.22 inches.

Devices of such type are described in the European patent EP 1332727 by Kozo Kawaguchi et al. published on Jun. 8, 2003 and also in the European patent EP 1350482 by Yoshiharu Shin et al. in which the base is cemented onto the labial face of the tooth, and in which the corrector wire does not have a closure element. In some cases this corrector wire remains attached and covered by an additional closure element, as disclosed in the European patent EP 1287789 by Masaaki Orikasa, published on May 3, 2003.

Some years ago, some devices appeared which were fixed onto the posterior surfaces of the teeth (over the lingual faces thereof). This technique has been called lingual orthodontics and an example of this technique is shown in the European patent EP 1405610 by Arthur Rosemberg published on Jul. 4, 2004.

All the systems previously mentioned have the inconvenience that they require the carrying out of a tying operation of the wire in the groove of the device in order to adjust the wire over the tooth, this inconvenience being eliminated with the present invention, since in the reverse bracket, the wire or treatment arch is not placed, like in the former cases at base level, but at the level of a new closure element called cap, which has a groove to lodge the wire, and furthermore some retention mechanisms that fit with the base.

GENERAL DESCRIPTION

The mechanical device of the present invention applies a new mechanical orthodontic system to transfer the forces of the wire onto the teeth. The innovative concept developed in the device is in the working system itself. The professional, instead of tying the wire into the devices' groove by means of metallic or elastic ties (conventional system), adjusts the wire onto the tooth by means of the fitting of the two main elements thereof (the cap onto the base). The wire will remain retained between them without the needing of having to be adjusted by means of the metallic or elastic ties.

Its clinical use in the mouth simplifies the handling, since by means of a simple pressure of the cap over the base, we adjust the corrector wire onto the tooth. Said cap has an active groove in which the treatment wire is inserted, and said active groove can have different torques (inclination of the tooth in the vestibular-lingual direction) and tips (mesiodistal inclination). What makes the difference of the present invention with respect to the brackets already existing, is the presence of the groove in the cap and not in the base. On the other hand, since the cap can be replaced over the base, fixed onto the tooth, and said base with invariable and fix torque and tip values at level of its active groove, it facilitates the interchange of caps. The torque is the inclination degree of said active groove with respect to the cap's base and the tip is the inclination of the tooth in relation to the midline. If we have a wide range of caps with different torques and tips (from degree to degree, from 0° up to 30° for example), we have the possibility to adjust the value of the torque and the tip according to the clinical requirements of the moment, by carrying out a simple interchange of the caps. The values of the torque and the tip of the caps will modify the existing values in the base by augmenting or diminishing them. Apart from its inclination, the groove may vary in width and caps can be used with width values of the groove of 0.018" or of 0.022", which allows the use of greater or smaller gauge or thickness.

The hemispherical shape of the assemblage (the cap is adjusted over it's base) introduces an optimized design that minimizes the possibility of frictions of the system. This confers a greater comfort to the patient.

Although the base is metallic, if the cap is all made of a material with a similar colour to that of the teeth, the aesthetic result of the assemblage will be optimal.

This kind of devices can also be used for the technique of lingual orthodontics, in which case its design will vary depending on the anatomical characteristics of the lingual or palatine faces of the teeth. The self-closing system with the pulling of the wire into the interior of the groove must allow an easier clinical handling of the technique.

DETAILED DESCRIPTION

The present invention shows a fundamental novelty over the orthodontics devices actually existing; said novelty is the existence of an active groove (8) which is located in the cap (3), and not in the base (2) which is usual in the mentioned patents of the actual state of the art. The treatment wire is inserted in said active groove (8), whereby said active groove (8) may have torques and tips at different angles (see FIG. 2). The base includes in its form the torque, the tip, the in/out (rotation of the tooth with respect to its axis) and the shape that adapts itself to the tooth by means of a retentive surface. As the cap (3) is coupled to the base (2) by means of retention mechanisms, it's easy to interchange the cap, or rather, to change the degree of torque and tip, according to the requirements of the moment for a determined orthodontic problem.

Figure 1:
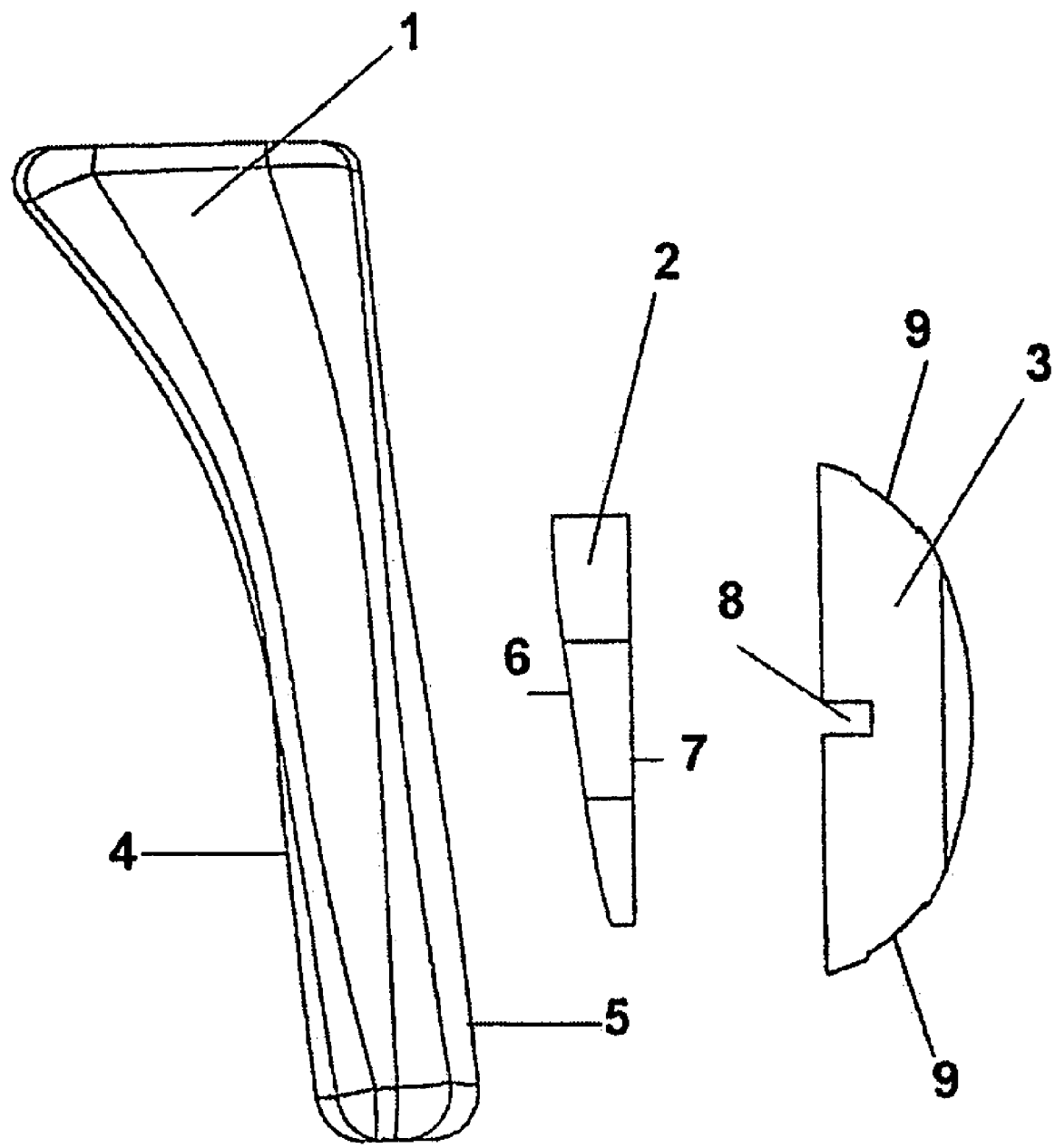
FIG. 1 is a side view the permits to see the relative position of the base and the tip with respect to the tooth. It is important to re-mark the position of the active groove located in the cap, which is the base of the present invention.

In the FIG. 1 there are shown the fundamental pieces of the present invention, in which there can be seen the tooth (1), the base (2) and the cap (3). The tooth (1) with its lingual face (4), and its labial face (5). The base (2) is cemented onto said tooth (1) with its lingual face (4), and it's a labial face (5). The base (2) is cemented onto said tooth (1) with its retentive surface (6) being the one which is cemented onto the tooth (1), and with its active surface (7), which is the one that is coupled to the cap (3). The cap (3) has the active groove (8), in which the orthodontic arch is inserted, and some coupling mechanisms (9) so that said cap (3) can be easily coupled to/released from the active surface (7) of the base (2).

The base (2) is cemented onto the tooth (1), and it is universal and shows a number of characteristics such as the torque or inclination of the tooth in the vestibular-lingual direction, tip or mesiodistal inclination, height or protrusion degree of the dental crown with respect to the other teeth, and rotation of the tooth in relation to its axial axis. Said morphological characteristics are invariable, and they correspond to average values, thereby existing a base for each tooth with fixed values of torque and tip, which are of the average values of the possible range (maximum and minimum value of the torque and the tip).

The base (2) shows, as said already, a retentive surface (6) to be fixed at the tooth, which shows an irregular form or "grid" form in order to facilitate its being cemented (glued) onto the tooth. The so-called active surface (7), is not in fact active, but rather is simply a contacting area with the cap. The reason why it has been called "active" is because it transmits the forces which the corrector wire introduces onto the cap (3) and is adhered to the tooth (1) by means of its adjustment on the base. The force application path is: →active groove (8) of the cap→body of the cap (3)→contact surface cap-base or active surface (7)→body of the base (2)→retentive area base/tooth or retentive surface (6)→tooth (1).

The cap (3) has as the most important part of the invention the active groove (8) in which the treatment wire is inserted and said active groove (8) can have different torques and tips. Therefore, caps should be with different characteristics (torque and tip), thereby being able to vary the standard effect of the base on the tooth.

Figure 2:
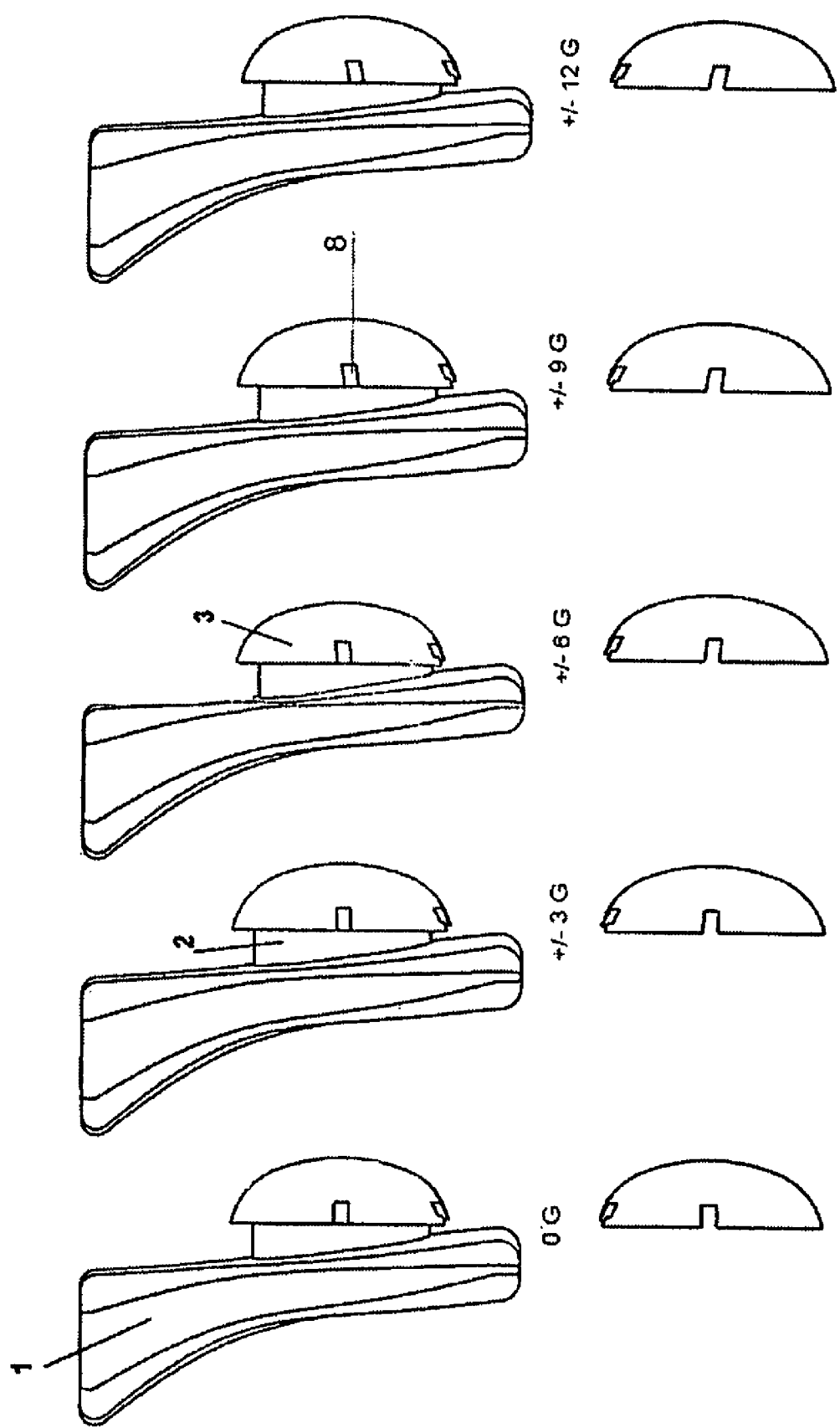
FIG. 2 is a set of side views which allow to see the tooth, base and cap at different angles of the torque/tip in the cap's groove.

As said before, the torque is variable in function of the cap (3) used, since caps are used with different torques, which can go from 0° up to 15° in increments of one degree, and which, depending on the position of the cap, will introduce into the axial inclination of the tooth a positive or negative torque, as can be seen in FIG. 2. In the same way, one may act in relation to the mesiodistal inclination or tip, by giving to the active groove different mesiodistal inclinations, that can go from 1° up to 12° in increments of one degree.

The base (2) and the cap (3) are joined by means of a retention system, whereby said retention system can be implemented in different ways that will depend both on the form of the base (2) as well as on the form of the cap (3), whereby both forms thereof must complement each other.

Figure 3:
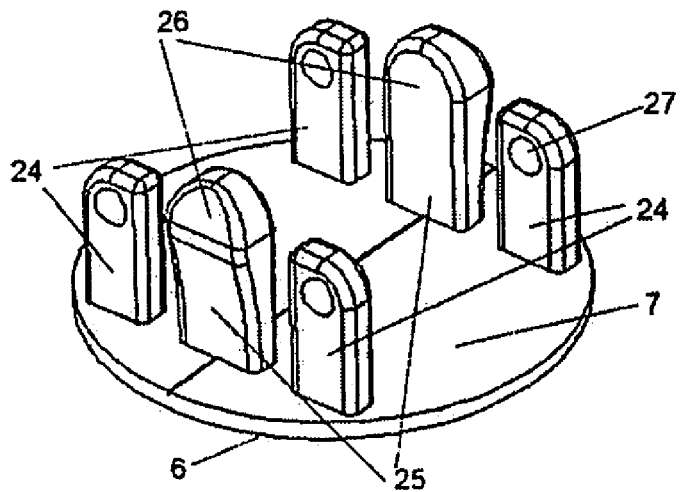
FIG. 3 is a perspective view of an embodiment of the base in which the retention flaps stand out.
Figure 4:
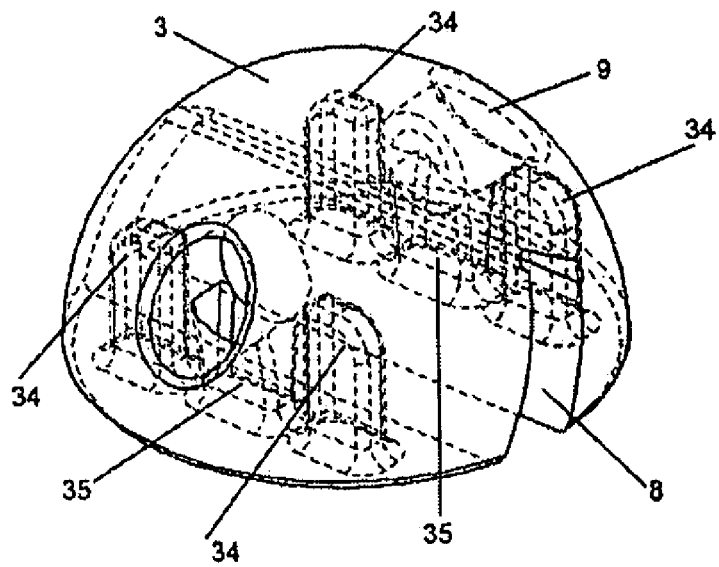
FIG. 4 is a perspective view of an embodiment of a complementary cap onto the base of FIG. 3 with it's reverse arch and retention grooves.
Figure 5:
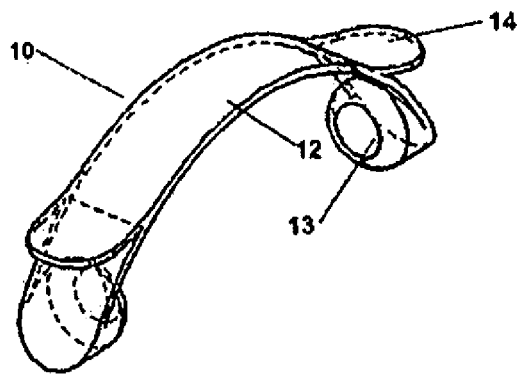
FIG. 5 is a perspective view of some auxiliary clips used for blocking/releasing the reverse bracket constituted by the base of the FIG. 3 and the cap of the FIG. 4.
Figure 6:
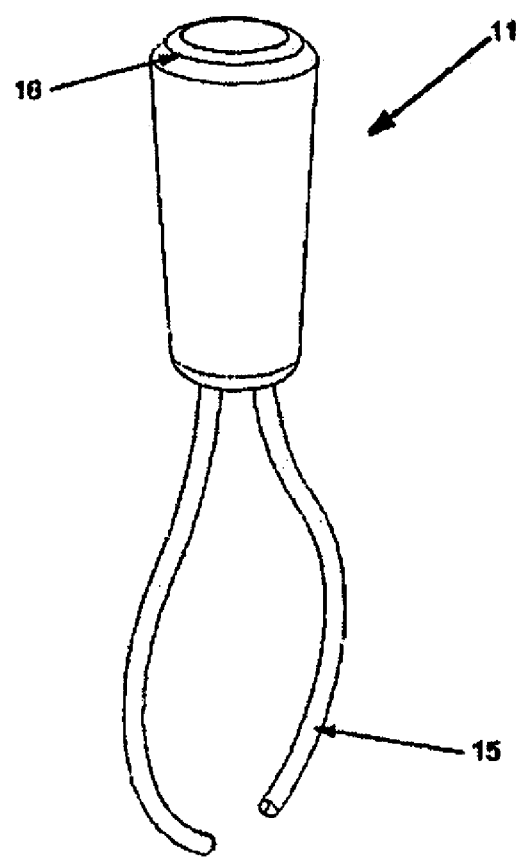
FIG. 6 is a perspective view of a tweezer used for blocking/releasing the arrangement of base-cap-clip of the foregoing drawings (FIGS. 3 to 5).

The FIGS. 3, 4, 5, and 6 show a first preferred embodiment of the present invention, the FIG. 3 shows the base (2), the FIG. 4 shows the cap (3), the FIG. 5 shows some retention clips between the base and the cap, of the FIGS. 3 and 4, and the FIG. 6 shows tweezers for the handling of the aforementioned members.

The base (2) can be of circular oval or rectangular shape and is composed of the following members:

a retentive surface (6) being able to be cemented onto the surface of the tooth;

an active surface (7), onto which is adapted the base of the cap (3) shown in the FIG. 4 and from which retentive wings emerge, each pair of them showing two stabilising tongues (24) and between them a retentive tongue (25) with a thickened finish of its end, which we shall call the end side of the retentive tongues (26), whereby each one of the stabilising tongues (24) shows a small retentive hole (27) in order to be able to pull the tooth by means of metallic ties if needed. The cap (3) has the shape of a hemisphere and incorporates the following elements:

an active groove (8) which is the essential part of the present invention and as said before, can have different angles with respect to the base in which the corrector wire is inserted. The active groove can either be simply carved into the material that forms the body of the cap (3) or show a metallic reinforcement, which will allow for a lesser friction with the orthodontic wire being used.

Some retentive grooves or elements, which can be of different shapes depending on the specific embodiment, but in a preferred embodiment are consisting of four grooves of stabilising tongues (34) destined to lodge the retentive tongues (25) of the base, two grooves of retentive tongues (35) destined to lodge the retentive tongues (25) of the base, and in the surface of the cap two lateral holes whose function is a double one: on one hand it serves as a retention of the ends of the retentive tongues (26), or on the other hand to favour the retention of the auxiliary clips which are detailed further on. The retention system can be diverse, depending on the direction in which the cap fits to the base. The retentive grooves or elements can be either in the base, or in the cap.

The auxiliary clips (10) have an elongated form and show the following characteristics:

The body (12), a part onto which this surface of the cap (3) is adhered.

The retentive ends (13) which are adjusted at the level of the lateral holes (9) of the surface of the cap (3). The arms (14), whose function is to facilitate the adjustment of elastics or retention wires. These arms may show ends of diverse forms, depending on their function or clinical utility. They serve to engage these active devices, such as elastics or elastic chains frequently used in orthodontics, whereby these arms can be a part of the cap or of the base, like fixed elements thereof (not removable).

The tweezer (11) is needed to be able to disengage the cap (3) from the base (2) by acting on the auxiliary clips (10). They show stoppers (15) at the level of the two ends thereof, which, by pressing at the level of the lateral holes (9) of the surface of the cap (3) on the retentive area of the ends of the retentive tongues (26) of the base (3), release the existing mechanical retention and thus allow the cap (3) to glide over the stabilising tongues (24) and set it off from the active surface (2) of the device's base (2). The posterior part of the tweezer (11) may show the form of a lever (16) to facilitate its use on the retentive ends (13) of the auxiliary clips (10), with the aim to unblock its fixation at the level of the lateral holes (9) of the surface of the cap (3). Said tweezers may have varied forms according to the retention mechanisms being used.

Figure 7:
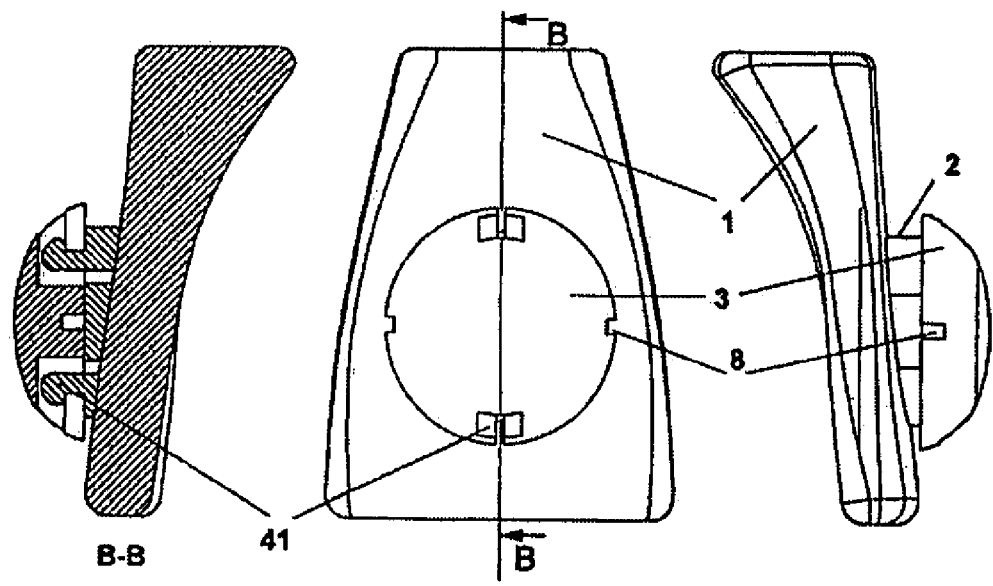
FIG. 7 shows a front view of an array of the tooth, base and cap in which the retention system is perpendicular to the vestibular surface of the tooth, with a view of a section of the axis through a perpendicular plane that shows a type of retention by a dovetail.
Figure 8:
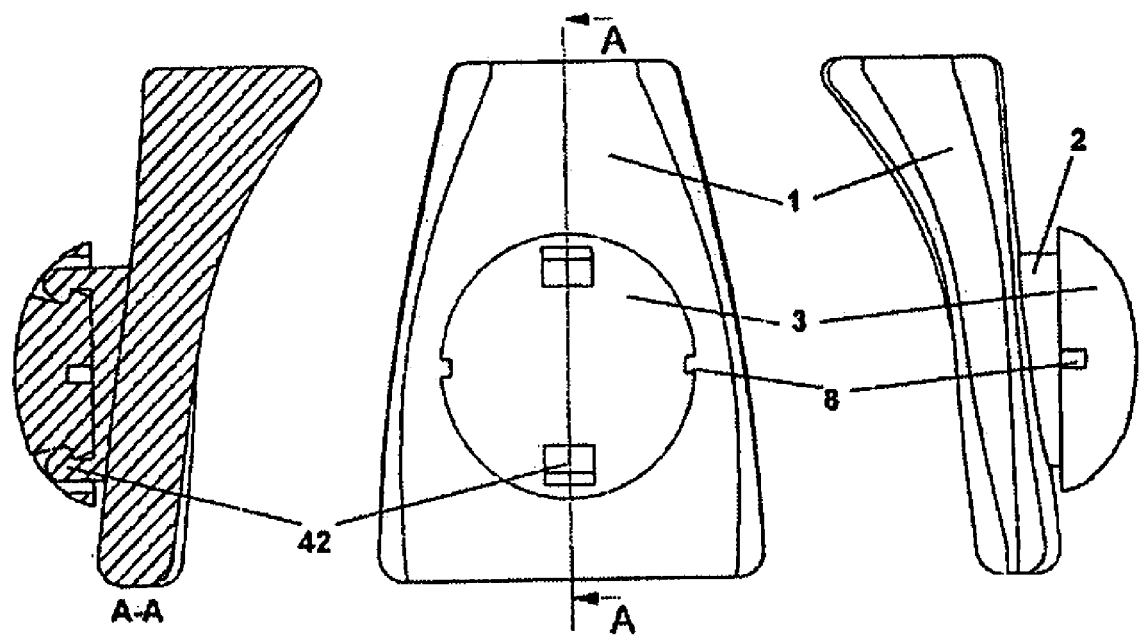
FIG. 8 shows a front view of an assembly of tooth base and cap in which the retention system is perpendicular to the vestibular surface of the tooth, with a section view of the axis through a perpendicular plane, that shows a retention type by means of a dovetail different from that of FIG. 7.
Figure 9:
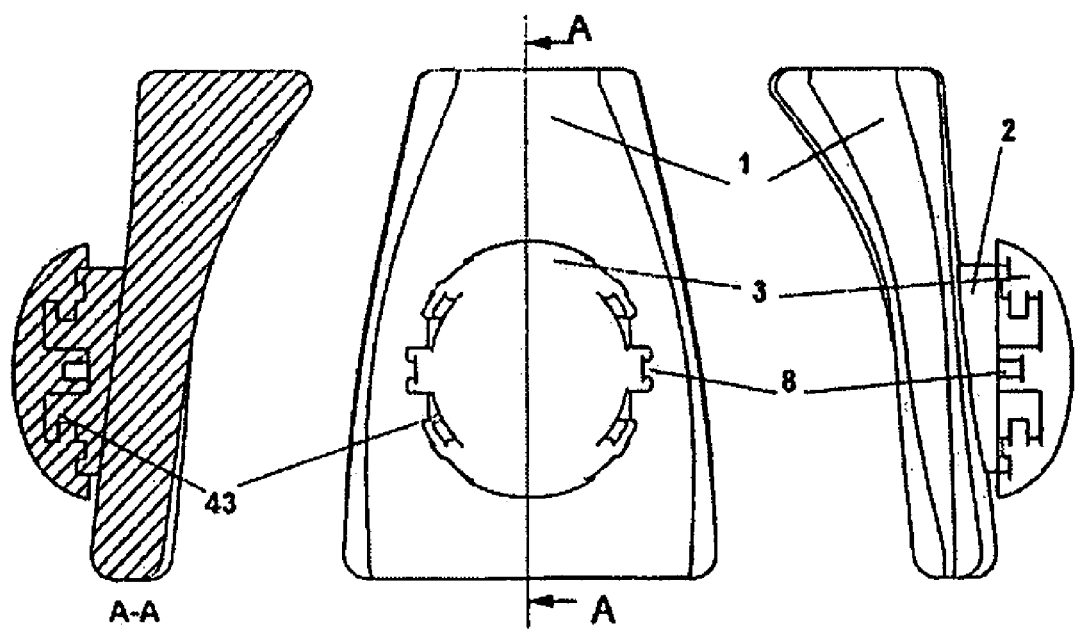
FIG. 9 shows a front view of an assembly of tooth, base and cap, in which the retention system is tangential to the vestibular surface of the tooth, with a section view in the perpendicular plane, and that shows a retention type by means of a dovetail.

Once the preferred embodiment has been described, it is yet to say that the fixation systems may be diverse and that other preferred embodiments could be made, such like those shown in FIGS. 7 to 9. In these drawings it can be seen that the retention is made through dovetails which can be positioned perpendicularly to the vestibular surface (FIGS. 7 to 8) or even tangentially to said surface of the tooth (FIG. 9), whereby one or the other is selected depending on the advantages of manufacture. In the FIG. 7 the retentive mechanism (41) is the dovetail, and in order to disengage it, it must be pressed inwards in parallel direction to the tooth, quite the contrary as with the retention mechanism (42) of the FIG. 8 which must be extracted outwards. In the FIG. 9 the retention mechanism (43) will be the disengaged by applying perpendicular forces to the surface of the tooth.

The previous description of the preferred embodiments is provided in order to allow to any person skilled in the art to produce or to use the present invention. Various modifications on these embodiments can be easily done by someone skilled in the art, and the generic principles herein defined can be applicable to other embodiments without falling out of the range of the present invention, as determined by the following claims:

The invention claimed is:

1. A mechanical device for use in orthodontics comprising:
   a base, having a retentive surface which is adapted to be attached to a tooth and an active surface;
   two pair of stabilizing tongues extending from said active surface and a pair of retentive tongues extending from said active surface between said pair of stabilizing tongues, and
   an interchangeable cap removably coupled to said base using a retention mechanism,
   said cap comprising four grooves for receiving said two pair of stabilizing tongues and two grooves for receiving said pair of retentive tongues, said cap having an active groove adapted for receiving a treatment wire, said active groove having a predetermined degree of torque and/or tip, thereby generating forces on said inserted treatment wire, said forces depending on an inclination degree of the active groove of the cap, said interchangeable cap allowing adjustment of the value for torque and/or tip according to clinical requirements during the orthodontic treatment.

2. The mechanical device of claim 1 wherein a width of the active groove can be of 0.018" or 0.022", thereby allowing said active groove to receive said treatment wire of a different size.

3. The mechanical device of claim 1 wherein said active groove is carved into a material that forms a body of the cap.

4. The mechanical device of claim 1 wherein said cap has the form of a hemisphere.

5. The mechanical device of claim 1 wherein each of said retentive tongues having a thickened end.

6. The mechanical device of claim 5 wherein said cap comprising on its surface two lateral holes for retention of the thickened ends of said retentive tongues.

7. The mechanical device of claim 6 wherein the retention mechanism is an auxiliary clip having an elongated form and a body on which the surface of the cap is a adhered, retentive ends of the auxiliary clip are adjusted at level of the lateral holes of the surface of the cap.

8. The mechanical device of claim 6 wherein the auxiliary clip includes arms extending from the auxiliary clip for facilitating the adjustment of the treatment wire.

9. The mechanical device of claim 1 further comprising an auxiliary tool for disengaging said cap from said base, a first end of said auxiliary tool including stoppers for pressing at the level of lateral holes of the surface of the cap to release the retention mechanism, thereby allowing the cap to slide over the stabilizing tongues and set it off from the active surface of the base.

10. The mechanism of claim 9 further comprising a lever at a second end of said auxiliary tool.

11. The mechanical device of claim 1, wherein the cap is formed of a color similar to that of the tooth.

* * * * *